(12) United States Patent
Gohl et al.

(10) Patent No.: US 9,028,740 B2
(45) Date of Patent: May 12, 2015

(54) PERMSELECTIVE MEMBRANE AND PROCESS FOR MANUFACTURING THEREOF

(71) Applicant: Gambro Lundia AB, Lund (SE)

(72) Inventors: Hermann Gohl, Bisingen (DE); Reinhold Buck, Alleshausen (DE)

(73) Assignee: Gambro Lundia AB, Lund (SE)

( * ) Notice: Subject to any disclaimer, the term of this patent is extended or adjusted under 35 U.S.C. 154(b) by 145 days.

(21) Appl. No.: 13/926,045

(22) Filed: Jun. 25, 2013

(65) Prior Publication Data

US 2013/0277878 A1    Oct. 24, 2013

Related U.S. Application Data

(62) Division of application No. 10/540,123, filed as application No. PCT/SE03/01985 on Dec. 17, 2003, now Pat. No. 8,496,122.

(30) Foreign Application Priority Data

Dec. 20, 2002 (SE) .................................. 0203857

(51) Int. Cl.
*B29D 99/00* (2010.01)
*B01D 67/00* (2006.01)
(Continued)

(52) U.S. Cl.
CPC ......... *B29D 99/005* (2013.01); *Y10T 428/2975* (2015.01); *A61M 1/16* (2013.01); *A61M 1/34* (2013.01); *B01D 67/0009* (2013.01);
(Continued)

(58) Field of Classification Search
None
See application file for complete search history.

(56) References Cited

U.S. PATENT DOCUMENTS

| 3,423,491 A | 1/1969 | Mahon et al. |
| 3,526,588 A | 9/1970 | Baker et al. |

(Continued)

FOREIGN PATENT DOCUMENTS

| EP | 0 082 433 | 12/1981 |
| EP | 0 168 783 | 1/1986 |

(Continued)

OTHER PUBLICATIONS

Office Action of U.S. Appl. No. 10/539,409 mailed on Mar. 14, 2011 (11 pages).

(Continued)

*Primary Examiner* — Monica Huson
(74) *Attorney, Agent, or Firm* — Barnes & Thornburg LLP (57) ABSTRACT

A method for preparing by solvent phase inversion spinning a hollow fiber membrane suitable for dialysis. The membrane includes at least one hydrophobic polymer and at least one hydrophilic polymer. An outer surface of the membrane is characterized by pores having sizes in the range of 0.5-3 µm, with the density of the pores on the outer surface of the membrane being in the range of 10,000 to 150,000 pores per mm². The method includes dissolving the at least one hydrophobic polymer and the at least one hydrophilic polymer in at least one solvent to form a polymer solution, extruding the thus-formed polymer solution through an outer ring slit of a nozzle with two concentric openings, extruding a center fluid through the inner opening of the nozzle, and wishing said membrane. The polymer solution coming out through the outer slit opening on the outside of the precipitating fiber is exposed to a humid steam/air mixture including a solvent content of between 0.5 and 10% by weight related to the water content.

19 Claims, 4 Drawing Sheets

(51) Int. Cl.

| | | |
|---|---|---|
| *B01D 69/02* | (2006.01) | |
| *B01D 69/08* | (2006.01) | |
| *D01D 5/24* | (2006.01) | |
| *A61M 1/16* | (2006.01) | |
| *A61M 1/34* | (2006.01) | |

(52) U.S. Cl.
CPC ........ *B01D67/0011* (2013.01); *B01D 67/0013* (2013.01); *B01D 69/02* (2013.01); *B01D 69/08* (2013.01); *B01D 2323/08* (2013.01); *B01D 2323/12* (2013.01); *B01D 2323/36* (2013.01); *B01D 2323/38* (2013.01); *B01D 2325/022* (2013.01); *D01D 5/24* (2013.01)

(56) References Cited

U.S. PATENT DOCUMENTS

| | | | |
|---|---|---|---|
| 3,615,024 | A | 10/1971 | Michaels |
| 4,399,035 | A | 8/1983 | Nohmi et al. |
| 4,664,669 | A | 5/1987 | Ohyabu et al. |
| 4,720,343 | A | 1/1988 | Walch et al. |
| 4,822,489 | A | 4/1989 | Nohmi et al. |
| 4,882,223 | A | 11/1989 | Aptel et al. |
| 4,935,141 | A | 6/1990 | Buck et al. |
| 4,938,778 | A | 7/1990 | Ohyabu et al. |
| 5,009,824 | A | 4/1991 | Walch et al. |
| 5,075,003 | A | 12/1991 | Aoyagi |
| 5,340,480 | A | 8/1994 | Kawata et al. |
| 5,505,851 | A | 4/1996 | Wagener et al. |
| 5,571,418 | A | 11/1996 | Lee et al. |
| 5,683,584 | A * | 11/1997 | Wenthold et al. ........ 210/500.23 |
| 5,707,522 | A | 1/1998 | Maeda et al. |
| 5,762,798 | A | 6/1998 | Wenthold et al. |
| 5,938,929 | A | 8/1999 | Shimagaki et al. |
| 6,045,899 | A | 4/2000 | Wang et al. |
| 6,565,782 | B1 | 5/2003 | Wang et al. |
| 6,802,820 | B1 | 10/2004 | Gorsuch et al. |
| 6,802,971 | B2 | 10/2004 | Gorsuch et al. |
| 6,890,435 | B2 | 5/2005 | Ji et al. |
| 8,136,675 | B2 | 3/2012 | Buck et al. |
| 2004/0060866 | A1 | 4/2004 | Radunsky et al. |
| 2004/0167237 | A1 | 8/2004 | Kim et al. |
| 2006/0144782 | A1 | 7/2006 | Buck |

FOREIGN PATENT DOCUMENTS

| | | |
|---|---|---|
| EP | 0 305 787 | 3/1989 |
| EP | 0 568 045 | 11/1993 |
| EP | 0568045 | 11/1993 |
| KR | 109507322 | 7/1995 |
| KR | 20010061733 | 7/2001 |
| WO | 86/00028 | 1/1986 |
| WO | 95/05887 | 3/1995 |
| WO | 9637282 | 11/1996 |
| WO | 01/78805 | 10/2001 |
| WO | 2004/056460 | 7/2004 |

OTHER PUBLICATIONS

Baker, R.W., et al.; (1991) Membrane Separation Systems-Recent Developments and Future Directions, )pp. 96-125, http://www.knovel.com/knovel2Toc.isp?BookID=312&VerticalID=0.

Combined Chemical Dictionary (2007), Triton X 100, http://ccd.chemnetbase.com/dictionary-search.do?method=view&id=510427.

Klein, E. et al., "Transport and Mechanical Properties of Hemodialysis Hollow Fibers", Journal of Membrane Science, 371-396, 1976.

International Search Report of International Application No. PCT/SE2003/001985, Apr. 2004.

Office Action from U.S. Appl. No. 10/539,409, dated Aug. 25, 2011, 9 pages.

"The Cytochrome c Protein", Downloaded from http://macromoleculeinsights.comcytochromec.php on Aug. 3, 2011.

"Basic Principles of Membrane Technology", 2$^{nd}$ Edition, Marcel Mulder, ed., 1996 Kluwer Academic Publishers, pp. 182-189.

Office Action of U.S. Appl. No. 10/539,409, mailed on Sep. 27, 2010 (7 pages).

Calvo, J et al., "Comparison of liquid-liquid displacement porosimetry and scanning electreon microscopy image analysis to characterize ultrafiltration track-etched membranes", Journal of Membrane Science, 239:189-198 (2004).

Capannelli, G. et al., "Ultrafiltration Membranes: Characterization Membranes", Journal of Membrane Science, 15:289-313 (1983).

International Standard ISO 8637, "Cardiovascular implants and artificial organs-Hemodialysers, haemodiafilters, haemofilters and haemocincentrators," Second Edition, Oct. 1, 2004.

Morgera, S. et al., "Intermittent high permeability hemofiltratiuon in septic patients with acute renal failure," Intensive Care Med., 29(11): 1989-1995 (2003).

Reabflo II Hemofilters leaflet, Minntech Therapeutic Technologies (2007).

Zusammenhang zwischen Spinntemperatur and Durchlassigkeit fur verschiedene Membranrezepturen (graph to demonstrate the spinning temperature effect), no date.

Comparison of properties between D3 (P170H) and a membrane according to the present invention (HCO 1100), attachment to Written Submission in preparation for oral proceedings for European Patent Application No. 03 781 225.2-2113, dated May 4, 2010.

Herbelin et al., "Elevated circulating levels of interleukin-6 in patients with chronic renal failure", Kidney International, vol. 39, (1991), pp. 954-960.

Office Action of U.S. Appl. No. 10/539,409, mailed on Apr. 14, 2009 (15 pages).

Deppisch et al., "Blood material interactions at the surfaces of membranes in medical applications", 1998, 14, pp. 241-254.

Office Action of U.S. Appl. No. 10/539,409, mailed on Feb. 23, 2010 (7 pages).

Office Action of U.S. Appl. No. 10/539,409, mailed on Oct. 15, 2009 (17 pages).

International Search Report for International Application No. PCT/SE2003/001993, dated Mar. 10, 2004.

\* cited by examiner

PERMSELECTIVE MEMBRANE AND PROCESS FOR MANUFACTURING THEREOF

CROSS REFERENCE TO RELATED APPLICATIONS

This application is a divisional of U.S. Ser. No. 10/540,123, filed Jun. 22, 2006, now U.S. Pat. No. 8,496,122. U.S. Ser. No. 10/540,123 is itself the U.S. national phase of PCT/SE2003/001985, filed Dec. 17, 2003. PCT/SE2003/001985 claims the benefit of the Dec. 20, 2002 filing date of Swedish patent application SE 0203857-8. The disclosures of all of SE 0203857-8, PCT/SE2003/001985 and U.S. Ser. No. 10/540,123 are hereby incorporated herein by reference.

TECHNICAL FIELD OF THE PRESENT INVENTION

The present invention relates to a permselective asymmetric hollow fiber membrane suitable for, for example, hemodialysis, to a process for manufacturing such a membrane and to the use thereof. The membrane according to the present invention comprises at least one hydrophobic polymer and at least one hydrophilic polymer.

Membranes of the above kind present special advantages when they are used in connection with different kinds of medical treatments, such as hemodialysis, hemofiltration and hemodiafiltration. They may, however, also be used in dialysis and filtration in general, for example in water purification or dehydration.

BACKGROUND OF THE INVENTION

Membranes of the above kind are described in detail in, for example, EP-A-0 568 045, EP-A-0 168 783, EP-B-0 082 433; and WO 86/00028. These membranes are manufactured from polymeric synthetic materials, they have asymmetric structure with high diffusive permeability (clearance) and have water filtration capability with ultrafiltration in the range of low flux to high flux. In EP-A-0 305 787, a 3-layer structure membrane and filter with corresponding performance, is disclosed.

The membranes according to prior art are well performing, but still have some space for improvement and optimization. The areas of improvable properties are that the fibers are difficult to handle, they stick together and adhere to each other, which cause problems during manufacturing of dialysers, specifically when potting them in polyurethane (PUR). Further, the permeability of the fibers is still improvable. Thus, the diffusive permeability (clearance) for different molecular weight substances in the range of urea can be improved, as well as to a higher extent the permeability for substances with middle molecular weight range, like $\beta_2$-M, factor D and others, but with low albumin permeability.

To achieve a high permeability for the substances with low and middle molecular weight on the one hand and on the other hand have a low permeability for albumin, is one of the requirements put on dialysis membranes. This characteristic is called "selectivity". The selectivity of prior art membranes still needs to be improved.

SUMMARY OF THE INVENTION

The object of the present invention is to improve hollow fiber membranes comprised of at least one hydrophobic polymer and at least one hydrophilic polymer, being suitable for, for example, hemodialysis. This object is achieved by a hollow membrane with an outer surface having pores in the size range of 0.5 to 3 μm and having number of said pores in the range of 10,000 to 150,000 pores per $mm^2$, preferably in the range of 18,000 to 100,000 pores per $mm^2$, most preferably 20,000 to 100,000 pores per $mm^2$.

A further object of the present invention is to provide a process for the preparation of the membrane according to the present invention.

This object is achieved by a solvent phase inversion spinning process, comprising the steps of a) said at least one hydrophobic polymer and said at least one hydrophilic polymer are dissolved in at least one solvent to form a polymer solution, b) said formed polymer solution is extruded through an outer ring slit of a nozzle with two concentric openings, c) a center fluid is extruded through the inner opening of the nozzle, thereafter d) said membrane is washed and preferably dried. According to the present invention the polymer solution coming out through the outer slit opening is, on the outside of the precipitating fiber, exposed to a humid steam/air mixture comprising a solvent in a content of between 0.5 and 10% by weight related to the water content.

Yet another object of the present invention is to provide use of the membrane according to the invention in hemodialysis, hemodiafiltration, hemofiltration, and in dialysis and filtration in general, for example for water purification or dehydration.

Other objects, features, advantages and preferred embodiments of the present invention will become apparent from the following detailed description when taken in conjunction with the enclosed scanning micrographs and the appended claims.

BRIEF DESCRIPTION OF THE DRAWINGS

Preferred embodiments of the present invention will now be described in more detail, reference bing made to the enclosed drawings, in which.

DETAILED DESCRIPTION OF THE INVENTION

The present invention improves the deficiencies of prior art membranes by a membrane with a unique outer surface of the hollow fiber membranes.

The outer layer is characterized by homogenous and open pore structure with a defined surface roughness. The openings of the pores are in the size range of 0.5-3 μm, further the number of said pores on the outer surface is in the range of 10,000 to 150,000 pores per $mm^2$, preferably in the range of 18,000 to 100,000 pores per $mm^2$, and most preferably in the range of 20,000 to 100,000 pores per $mm^2$. In the enclosed scanning micrographs you can see micropgraph pictures of the outer surface of a hollow fiber according to the invention (FIG. 1 and FIG. 2), where you clearly see the pores of the outer surface. In FIG. 3, you can see the outer surface of a hollow fiber, which is not according to the invention.

An outer surface like the one according to the present invention provides for many advantages.

One advantage is that it provides for a hollow fiber membrane, which is non-sticky and is easy to handle. This leads to less cracks and holes in the fibers during the manufacturing process, which in turn leads to less scrap in the manufacturing process.

Another advantage is that the hollow fiber has less tendency to adhere to the hollow fibers lying close to it in the bundle, this due to the high numbers of said pores over the surface. Thus, the dialysate surrounding the hollow fibers during use has enhanced access to the hollow fibers when they are less inclined to adhere to each others, and during the potting of the hollow fibers the potting material, usually PUR, also has enhanced access to the individual hollow fibers providing a proper and more reliable potting around each hollow fiber.

Still another advantage is that the high numbers of said pores gives enhance access for the polyurethane (PUR) during potting to penetrate through the membrane outside part into the structure of the membrane. The penetration of PUR into the structure gives a safe fixation of the membrane and herewith a leakage free potting of fibers.

This specific surface on the outside of the hollow fiber is achieved by modifying the spinning polymer solution composition only in the outer section of the hollow fiber membrane wall by penetration of water from a very specific steam/air/solvent atmosphere into the first 1-15 μm of polymer solution layer just before the precipitation from the inside arrives at this layer. The penetration occurs in less than 0.5 seconds.

Figure 4:
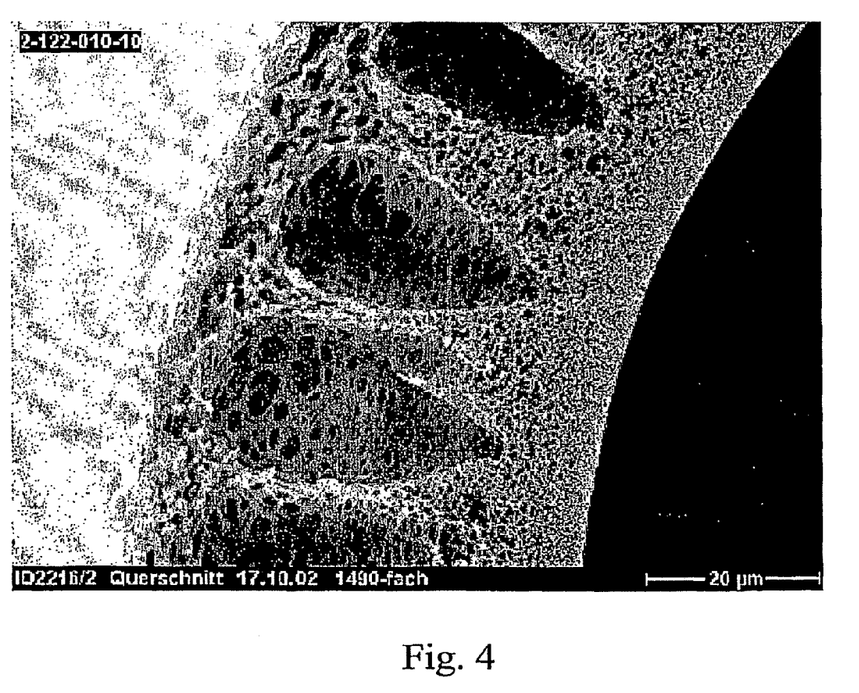
FIG. 4 shows a scanning electron microscopic picture of a cross section of the membrane structure according to a preferred embodiment of the invention.

The surrounding of the fiber when the fiber is built up after the nozzle needs determined conditions, like humidity, temperature, volume of steam flux, defined selected composition of the polymer solution, viscosity, temperature and a certain composition and condition of the center fluid. This from two sides performed precipitation of the fiber (from the inner and outer side) allows achieving the structure as described above. In a preferred embodiment of the present invention, the membrane has a unique and very specific four-layer structure having a diffusive permeability of urea of $15$-$17 \times 10^{-4}$ cm/sec measured at 37° C. The diffusive permeability was measured according to E. Klein, F. Holland, A. Lebeouf, A. Donnaud, J. K. Smith, "Transport and Mechanical Properties of Hemodialysis Hollow Fibers", Journal of Membrane Science 1 (1976) 371-396, especially pages 375-379. In FIG. 4, a scanning micrograph is shown over this preferred four-layer structure. The inner layer of the four-layer structure, i.e. the blood contacting layer and the inner surface of the hollow fiber membrane, is a separation layer in form of a dense rather thin layer having, in a preferred embodiment, a thickness less than 1 μm and a pore size in the nano-scale range. To achieve high selectivity the pore channels with the responsible pore diameters are short (<0.1 μm). The pore channel diameter has a very low variation in size.

Pore size can be made in different ranges, e.g. for a low flux membrane in the range of 5-10 nm, and for a high flux membrane between 5 and 20 nm, preferably 7 to 12. This different pore size creates a membrane which has a cut off e.g. for low flux of about 5,000 Dalton and for high flux of about 40,000 Dalton in the presence of whole blood. The cut off is defined as a molecular weight, which is rejected by the membrane. The defined pore structure is achieved by selection of the composition of the polymer, the composition and condition of the precipitation media in the center fluid and by the condition and composition of the surrounding environment of the fiber leaving the spinning nozzle.

The next layer in the hollow fiber membrane is the second layer having the form of a sponge structure and, in a preferred embodiment of the present invention, a thickness of about 1 to 15 μm and serving as a support for said first layer. Then, there is the third layer having the form of a finger structure. It provides like a framework a mechanical stability on the one hand; on the other hand it has through the high void volume a very low resistance of transport of molecules through the membrane. During the process the voids are filled with water and the water gives a lower resistance for diffusion and convection than a matrix with a sponge-filled structure having a lower void volume. Accordingly, the third layer gives the membrane a mechanical stability and has, in a preferred embodiment of the present invention, a thickness of 20 to 60 μm.

The fourth layer in this preferred embodiment of the present invention is the outer layer, with the outer surface according to above. This fourth layer has in a preferred embodiment a thickness of about 1 to 10 μm.

This four-layer design together with the avoiding of fiber cracks and leakages give a high selectivity, which means, a high potential to separate molecules, which are close in their size, for example, to separate albumin from $\beta_2$-microglobulin and Factor D.

A preferred embodiment of the membrane according to the present invention consists of 65-95% by weight of said at least one hydrophobic polymer and 5-35% by weight of said at least one hydrophilic polymer.

Said at least one hydrophobic polymer is preferably chosen from the group consisting of polyamide (PA), polyaramide (PAA), polyarylethersulphone (PAES), polyethersulphone (PES), polysulphone (PSU), polyarylsulphone (PASU), polycarbonate (PC), polyether, polyurethane (PUR), polyetherimide and copolymers of said polymers, preferably polyethersulphone or a mix of polyarylethersulphone and polyamide.

Said at least one hydrophilic polymer is preferably chosen from the group consisting of polyvinylpyrrolidone (PVP), polyethylene glycol (PEG), polyglycolmonoester, water soluble cellulosic derivates, polysorbate and polyethylene-polypropylene oxide copolymers, preferably polyvinylpyrrolidone.

In a preferred embodiment of the process according to the present invention the temperature of the humid steam/air mixture is at least 15° C., preferably at least 30° C., and at most 75° C., preferably at most 60° C.

Further, the relative humidity in the humid steam/air mixture is between 60 and 100%.

In preferred embodiment of the present invention the humid steam/air mixture comprise a solvent in a content of between 0.5 and 5% by weight related to the water content.

In an even more preferred embodiment of the present invention the humid steam/air mixture comprise a solvent in a content of between 2 and 3% by weight related to the water content.

The effect of the solvent in the temperature controlled steam atmosphere is to control the speed of precipitation of the fibres. If less solvent is employed the outer surface will obtain a more dense surface, and if more solvent is used the outer surface will be more open structure. By controlling the amount of solvent within the temperature controlled steam atmosphere surrounding the precipitating membrane, the amount and size of the pores on the outer surface of the membrane are controlled, i.e. the size of the openings of the pores are in the range of 0.5-3 μm and the number of said pores are in the range of 10,000 to 150,000 pores per $mm^2$, preferably 18,000 to 100,000 pores per $mm^2$, and most preferably 20,000 to 100,000 pores per $mm^2$.

The polymer solution, used in the process of the present invention preferably consists of 10-20% by weight of the at least one hydrophobic polymer, 3-11% by weight of the at least one hydrophilic polymer, 66-86% by weight solvent and 1-5% by weight suitably additives. Suitably additives comprise for example in one preferred embodiment coagulation fluid chosen form the group of water, glycerol and/or other alcohols.

The solvent, used in the process of the present invention preferably is chosen from the group comprising n-methylpyrrolidon (NMP), dimethylacetamide (DMAC), dimethylsulphoxide (DMSO), dimethylformamide (DMF), butyrolactone and mixtures of said solvents.

In one preferred embodiment said center fluid includes a part of said at least one hydrophilic polymer. Further, it could include at least one of the above-mentioned solvents and precipitation medium chosen from the group of water, glycerol and other alcohols. Most preferably the center fluid consist of 45-70% by weight precipitation medium, 30-55% by weight of solvent and 0-5% by weight of said at least one hydrophilic polymer.

The present invention will now be described in more detail in the examples below. The examples are only given by way of illustration and are not to be interpreted as limiting the scope of protection of the present invention.

Example 1

A polymer solution is prepared by mixing 13.5% of polyarylethersulphone, 0.5% of polyamide, 7.5% of PVP K30 and 78.5% of NMP. A mixture of 59% water and 41% NMP serves as center fluid. The viscosity of the polymer solution, measured at a temperature of 22° C., is 4,230 mPas.

Center fluid is heated to 55° C. and pumped towards a two-component hollow fiber spinneret. The polymer solution is leaving the spinneret through an annular slit with an outer diameter of 0.5 mm and an inner diameter of 0.35 mm. The center fluid is leaving the spinneret in the center of the annular polymer solution tube in order to start the precipitation of the polymer solution from the inside and to determine the inner diameter of the hollow fiber.

At the same time the two components (polymer solution and center fluid) are entering a space separated from the room atmosphere. The space is called spinning shaft. A mixture of steam (100° C.) and air (22° C.) is injected into the spinning shaft. The temperature in the spinning shaft is adjusted by the ratio of steam and air at 49° C. and a relative humidity of 99.5% and the solvent content therein was adjusted to 3.9% by weight related to the water content. The solvent was NMP. The length of the spinning shaft is 890 mm. By the aid of gravity and a motor-driven roller, the hollow fiber is drawn from top to bottom, from spinneret through the spinning shaft into a water bath in vertical direction. The spinning velocity is 50 m/min. The hollow fiber is subsequently led through a cascade of water bathes and temperatures increasing from 20 to 90° C. The wet hollow fiber membrane leaving the water-rinsing bath is dried in a consecutive online drying step. After a texturizing step, the hollow fiber is collected on a spinning wheel in the shape of a bundle. After introducing the bundle into a dialyser housing, it is potted with polyurethane, ends are cut, on both sides of the dialyser a header is fixed to the housing, the dialyser is rinsed with hot water and dried with air. During this last drying step, an amount of 17 g of residual water per m$^2$ effective membrane area is left on the dialyser. After labeling and packaging, the dialyser is steam-sterilized within the package in an autoclave at 121° C. for 25 min.

Figure 1:
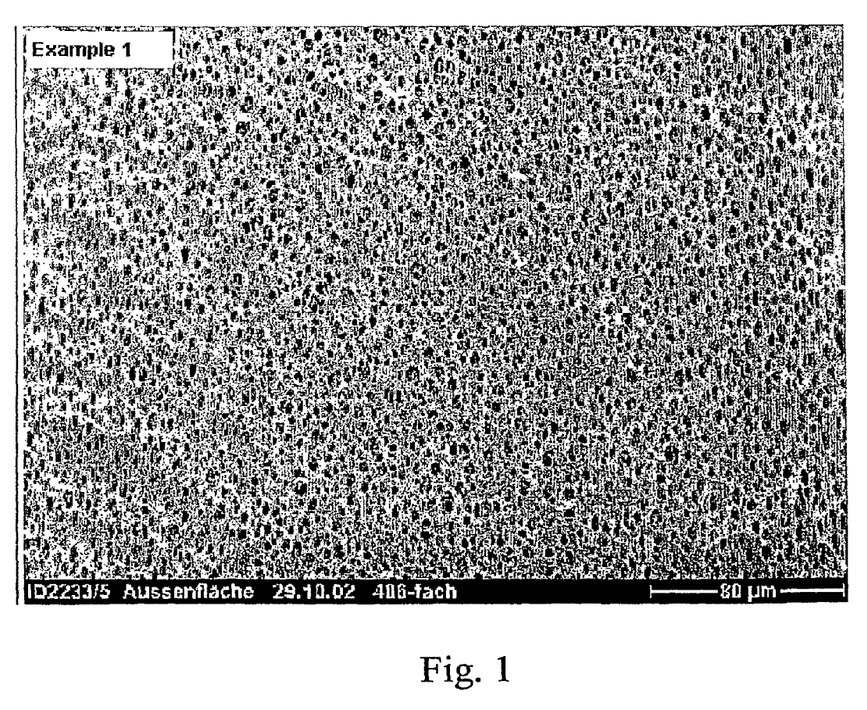
FIGS. 1 and 2 show scanning electron microscopic pictures of the outer surface of membranes according to preferred embodiments of the present invention.

A scanning micrograph of the outer surface of the hollow fiber according to example 1 is shown in FIG. 1. The hollow fiber according to this example had 62,500 pores in the range of 0.5 to 3 μm per mm$^2$.

Example 2

Hollow fibers were manufactured according to example 1 with the exception that less steam was used in the spinning shaft. The temperature in the spinning shaft was adjusted by the ratio of steam and air at 37° C. and a relative humidity of 84%. The content of solvent NMP) was adjusted to 2.4% by weight related to the water content.

Figure 2:
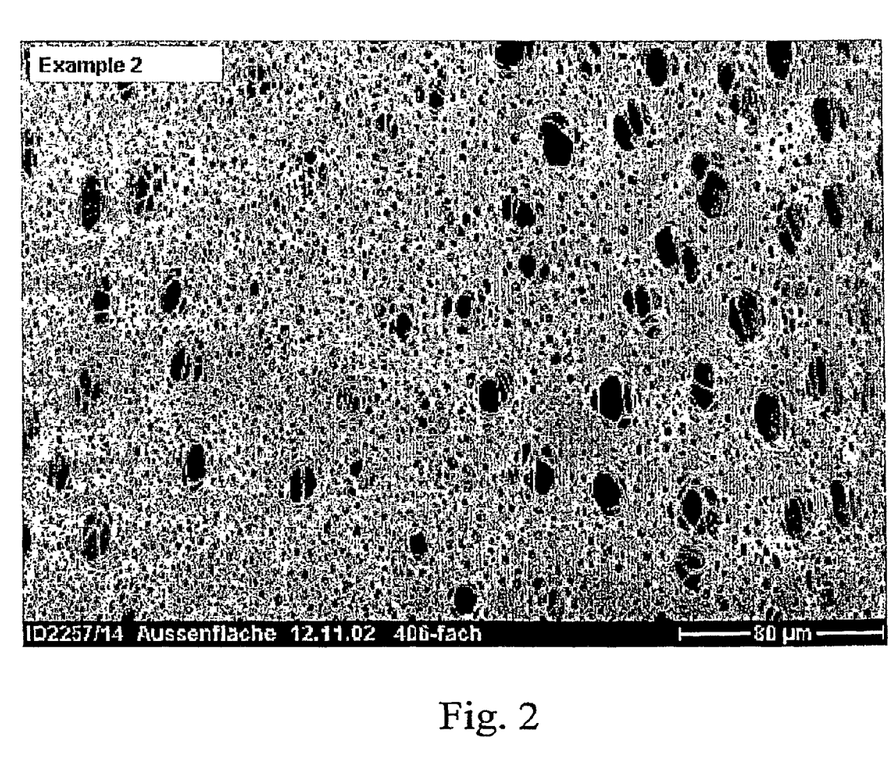
Figure 3:
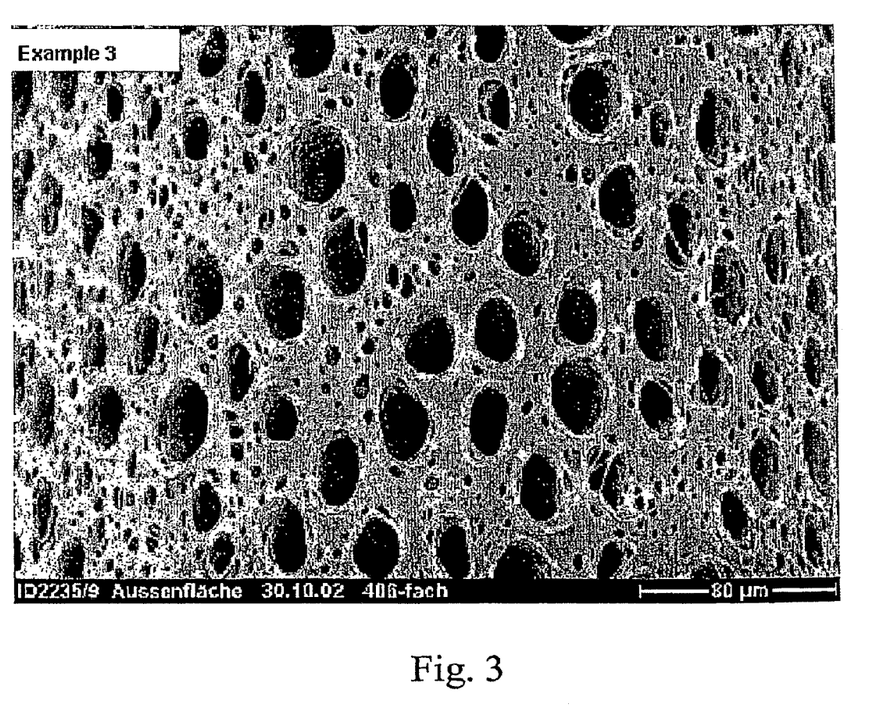
FIG. 3 shows a scanning electron microscopic picture of the outer surface of a comparative membrane.

A scanning micrograph of the outer surface of the hollow fiber according to example 2 is shown in FIG. 2. The hollow fiber according to this example had 18,700 pores in the range of 0.5 to 3 μm per mm$^2$.

Example 3 (Comparative)

Hollow fibers were manufactured according to example 1 with the exception that no steam was used in the spinning shaft. The temperature in the spinning shaft was 26° C. and the relative humidity was 55%.

A scanning micrograph of the outer surface of the hollow fiber according to example 3 is shown in FIG. 3.

The hollow fiber according to this example had 3,650 pores in the range of 0.5 to 3 μm per mm$^2$.

The hollow fibers produced according to the examples 1 to 3 were then evaluated concerning scrapped fibers bundles, clearance urea and selectivity myoglobulin/albumin. The results are presented in the table below.

The method used for determining clearance urea and selectivity myoglobulin/albumin (by measuring sieving coefficients) was EN 1283.

Examples 1 and 2 are according to the invention, while example 3 not is according to the invention and is only given for comparison.

| Example | Scrapped fiber bundles (%) | Clearance urea ml/min | Selectivity myoglobulin-/albumin |
| --- | --- | --- | --- |
| 1 | 0.1 | 272 | 16 |
| 2 | 6 | 252 | 8 |
| 3 | 48 | 208 | 5 |

The advantages of the membrane according to the present invention over prior art are that it has higher selectivity, higher diffusive permeability, improved handling properties, improved potting properties, high versatility for different types of membranes (low flux, mid flux and high flux etc.) and shows a higher rate of defect-free fibers, although there are high asymmetries and high numbers of weight in the membrane structures.

It will be readily apparent to one skilled in the art that various substitutions and modifications may be made to the present invention disclosed herein without departing from the scope and spirit of the present invention.

The invention claimed is:

1. A method for preparing by solvent phase inversion spinning a hollow fiber membrane suitable for dialysis, the membrane comprising at least one hydrophobic polymer and at least one hydrophilic polymer, an outer surface of the membrane having pores having sizes in the range of 0.5-3 μm, the density of said pores on the outer surface being in the range of 10,000 to 150,000 pores per mm$^2$, the method comprising:

dissolving said at least one hydrophobic polymer and said at least one hydrophilic polymer in at least one solvent to form a polymer solution, extruding said formed polymer solution through an outer ring slit of a nozzle with two concentric openings, extruding a center fluid through the inner opening of the nozzle, and washing said membrane, wherein the polymer solution coming out through the outer slit opening is, on the outside of the precipitating fiber, exposed to a humid steam/air mixture comprising a solvent in a content of between 0.5 and 10% by weight related to the water content, the polymer solution consisting of 10-20% by weight of the at least one hydrophobic polymer, 3-11% by weight of the at least one hydrophilic polymer, 66-86% by weight solvent, and 1-5% by weight suitable additives.

2. The process according to claim 1 wherein the solvent content within the humid steam/air mixture is between 0.5 and 5% by weight related to the water content.

3. The process according to claim 1 wherein the solvent content within the humid steam/air mixture is between 2 and 3% by weight related to the water content.

4. The process according to claim 1 wherein the temperature of the humid steam/air mixture is at least 15° C. and not more than 75° C.

5. The process according to claim 1 wherein the relative humidity in the humid steam/air mixture is between 60 and 100%.

6. The process according to claim 1 wherein the polymer solution comprises 1-5% by weight coagulation fluid chosen from the group consisting of water, glycerol, and other alcohols.

7. The process according to claim 1 wherein said solvent is chosen from the group consisting of n-methylpyrrolidone (NMP), dimethylacetamide (DMAC), dimethylsulfoxide (DMSO), dimethylformamide (DMF), buturolactone, and mixtures of these.

8. The process according to claim 1 wherein said center fluid includes at least one solvent chosen from the group consisting of n-methylpyrrolidone (NMP), dimethylacetamide (DMAC), dimethylsulfoxide (DMSO), dimethylformamide (DMF), butyrolactone, and mixtures of these.

9. The process according to claim 1 wherein said center fluid includes precipitation medium chosen from the group consisting of water, glycerol, and other alcohols.

10. The process according to claim 1 wherein the membrane is dried following the washing step.

11. The process according to claim 1 wherein the temperature of the humid steam/air mixture is at least 30° C. and not greater than 60° C.

12. The process according to claim 2 wherein the temperature of the humid steam/air mixture is at least 15° C. and not more than 75° C.

13. The process according to claim 3 wherein the temperature of the humid steam/air mixture is at least 15° C. and not more than 75° C.

14. The process according to claim 2 wherein the relative humidity in the humid steam/air mixture is between 60 and 100%.

15. The process according to claim 3 wherein the relative humidity in the humid steam/air mixture is between 60 and 100%.

16. The process according to claim 4 wherein the relative humidity in the humid steam/air mixture is between 60 and 100%.

17. A method for preparing by solvent phase inversion spinning a hollow fiber membrane suitable for dialysis, the membrane comprising at least one hydrophobic polymer and at least one hydrophilic polymer, an outer surface of the membrane having pores having sizes in the range of 0.5-3 µm, the density of said pores on the outer surface being in the range of 10,000 to 150,000 pores per mm$^2$, the method comprising:

dissolving said at least one hydrophobic polymer and said at least one hydrophilic polymer in at least one solvent to form a polymer solution, extruding said formed polymer solution through an outer ring slit of a nozzle with two concentric openings, extruding a center fluid through the inner opening of the nozzle, and washing said membrane, wherein the polymer solution coming out through the outer slit opening is, on the outside of the precipitating fiber, exposed to a humid steam/air mixture comprising a solvent in a content of between 0.5 and 5% by weight related to the water content, the polymer solution consisting of 10-20% by weight of the at least one hydrophobic polymer, 3-11% by weight of the at least one hydrophilic polymer, 66-86% by weight solvent, and 1-5% by weight suitable additives.

18. A method for preparing by solvent phase inversion spinning a hollow fiber membrane suitable for dialysis, the membrane comprising at least one hydrophobic polymer and at least one hydrophilic polymer, an outer surface of the membrane having pores having sizes in the range of 0.5-3 the density of said pores on the outer surface being in the range of 10,000 to 150,000 pores per mm$^2$, the method comprising:

dissolving said at least one hydrophobic polymer and said at least one hydrophilic polymer in at least one solvent to form a polymer solution, extruding said formed polymer solution through an outer ring slit of a nozzle with two concentric openings, extruding a center fluid through the inner opening of the nozzle, and washing said membrane, wherein the polymer solution coming out through the outer slit opening is, on the outside of the precipitating fiber, exposed to a humid steam/air mixture comprising a solvent in a content of between 0.5 and 10% by weight related to the water content, said center fluid including a part of said at least one hydrophilic polymer.

19. A method for preparing by solvent phase inversion spinning a hollow fiber membrane suitable for dialysis, the membrane comprising at least one hydrophobic polymer and at least one hydrophilic polymer, an outer surface of the membrane having pores having sizes in the range of 0.5-3 µm, the density of said pores on the outer surface being in the range of 10,000 to 150,000 pores per mm$^2$, the method comprising:

dissolving said at least one hydrophobic polymer and said at least one hydrophilic polymer in at least one solvent to form a polymer solution, extruding said formed polymer solution through an outer ring slit of a nozzle with two concentric openings, extruding a center fluid through the inner opening of the nozzle, and washing said membrane, wherein the polymer solution coming out through the outer slit opening is, on the outside of the precipitating fiber, exposed to a humid steam/air mixture comprising a solvent in a content of between 0.5 and 10% by weight related to the water content, said center fluid consisting of 45-70% by weight precipitation medium, 30-55% by weight solvent, and less than or equal to 5% by weight said at least one hydrophilic polymer.

* * * * *